United States Patent
Westwood

(12)
(10) Patent No.: US 6,696,577 B1
(45) Date of Patent: Feb. 24, 2004

(54) METHOD OF PRODUCING ORGANIC ACIDS FOR USE AS AN ELECTROLYTE IN PRODUCING HIGH IONIZATION CONCENTRATIONS OF PRECIOUS METALS

(75) Inventor: Kenneth D. Westwood, Diamond Valley, UT (US)

(73) Assignee: The Chemins Company, Inc., Colorado Springs, CO (US)

( * ) Notice: Subject to any disclaimer, the term of this patent is extended or adjusted under 35 U.S.C. 154(b) by 22 days.

(21) Appl. No.: 10/254,145

(22) Filed: Sep. 24, 2002

Related U.S. Application Data

(62) Division of application No. 09/801,477, filed on Mar. 7, 2001, now Pat. No. 6,478,946, which is a continuation-in-part of application No. 09/119,741, filed on Jul. 21, 1998, now abandoned, which is a division of application No. 08/583,675, filed on Jan. 5, 1996, now abandoned.

(51) Int. Cl.$^7$ ............................................. C07D 319/10
(52) U.S. Cl. ........................................................ 549/359
(58) Field of Search ......................................... 549/359

(56) References Cited

U.S. PATENT DOCUMENTS

| | | | |
|---|---|---|---|
| 2,785,153 A | | 3/1957 | Locke .......................... 260/114 |
| 2,785,154 A | | 3/1957 | Locke .......................... 260/114 |
| 4,592,814 A | | 6/1986 | Vaughan et al. ............... 204/78 |
| 4,855,494 A | * | 8/1989 | Margureanu et al. ........ 562/580 |
| 5,346,624 A | * | 9/1994 | Libutti et al. ................ 210/679 |

OTHER PUBLICATIONS

Westwood, K.D., Patent appln 09/119,741, filed on Jul. 21, 1998, with §132 declaration dtd May 1, 2000.

Aitken, et. al., The Characteristics and Effects of Humic Acids Derived from Leonardite, Technical Bulletin 1015, pp. 204–207, S. Carolina Agriculture Experimental Station, Clemson Univ., Clemson, SC.

Becker, R.O., Cross Currents, pp. 163–166, Jeremy P. Tarcher, Inc., Publisher, Los Angeles, CA.

Jackson, W.R., Humic, Fulvic and Microbial Balance: Organic Soil Conditioning, , pp. 204–221, 250, 262–262, 270, Jackson Research Center Publisher, Evergreen, CO.

Reddish, G.F., Antiseptics, Disinfectants, Fungicides, and Chemical and Physical Sterilization, pp. 470–477, 482–491, Lea & Febiger Publisher, Philadelphia, PA.

Sheludko, A., Colloid Chemistry, pp. 8–11, 148–153, Elsevier Publishing Co., New York, NY.

Svedberg, T., The Formation of Colloids, pp. 18–53, D. Van Nostrand Co. Publisher, New York, NY.

Ansorg, R., et al., , "Studies on the Antimicrobial Effect of Natural and Synthetic Humic Acids", CAPLUS Abstract 90:67143, 1979.

Cronje, I.J. et. al., "Bactericidal Coal–Derived Fulvic Acids", CAPLUS Abstract 116:78586, 1992, and "Bacteriostatic and Bacteriocidal Method Using Fulvic Acid Derivatives; Water Treatment, Particularly Aqueous Solutions for Cascading Plates in Industrial Cooling Towers", IFIPAT Abstract, 2000 (U.S. patent 5,204,368).

Cronje, I.J. et al., "Humic Acids as Bactericides", CAPLUS Abstract 112:231293, 1990.

Fisher E.I., et. al., "Nature of the Interaction of Natural Organic Acids with Gold", CAPLUS Abstract 82:19513, 1975.

Fujimura Y., et. al.,, "Inhibitory Action of Dissolved Humic Substances on the Growth of Soil Bacteria Degrading DDT", JICST–EPlus Abstract, 940–797–033, 2000.

Mahasneh, A., et. al., "Some Features and Antimicrobial Activity of Humic Acid Isolated From Jordanian Soils", CAPLUS Abstract 111:193605, 1989.

Schnitzer, M., et. al., "Binding of Humic Substances by Soil Mineral Colloids", CABA Abstract 86:93420, 1986.

Wood, S.A., "The Interaction of Dissolved Platinum with Fulvic Acid and Simple Organic Acid Analogues in Aqueous Solutions", CAPLUS Abstract 114:85937, 1991.

* cited by examiner

Primary Examiner—Joseph K. McKane
Assistant Examiner—Kamal Saeed
(74) Attorney, Agent, or Firm—Frank G. Morkunas

(57) ABSTRACT

A method of preparing organic acids (fulvic, humic, and ulmic) for use as an electrolyte for producing high ionizations of precious metals (such as silver) which entails leaching out the organic acid from its source, stabilizing the organic acid first with ascorbic acid followed by sodium benzoate, removing cations, and using the organic acid as an electrolyte. A precious metal (such as silver) is used as a sacrificial electrode in this electrolyte. A non-sacrificial electrode could either be the same precious metal or an inert non-precious metal (titanium or graphite carbons). If the same material is used for the non-sacrificial electrode as for the sacrificial electrode, the size of each electrode may be about the same. If different material is used for the non-sacrificial electrode, its size should be larger that of the sacrificial electrode. Current at about 2 or more volts is applied to the electrodes and the ionization process begins yielding high concentrations of ionized precious metals.

6 Claims, No Drawings

METHOD OF PRODUCING ORGANIC ACIDS FOR USE AS AN ELECTROLYTE IN PRODUCING HIGH IONIZATION CONCENTRATIONS OF PRECIOUS METALS

CROSS-REFERENCES AND RELATED APPLICATIONS

This application is a divisional application to my previously filed application, Ser. No. 09/801,477, filed on Mar. 7, 2001 now U.S. Pat. No. 6,478,946 for an invention which is a continuation-in-part to my previously filed application, Ser. No. 09/119,741, filed on Jul. 21, 1998 now abandoned, which was a divisional application of application Ser. No. 08/583,675 filed on Jan. 5, 1996 now abandoned.

BACKGROUND OF THE INVENTION

This invention relates to improved methods to generate silver colloids (and colloids from other precious metals) and to thereby generate greater concentrations of ionized silver (and ionized solutions of other precious metals) from specially prepared organic acids such as fulvic acid, humic acid, or ulmic acid or combinations thereof.

Colloidal silver has been produced by precipitating silver from a silver nitrate or other toxic chemical solutions which may contain silver. One example of this process is disclosed by Locke, et al., in U.S. Pat. Nos. 2,785,154 and 2,785,153 wherein silver protein crystals are made by a chemical reaction with their improvement being a chelating agent. This, however, yields a toxic result.

Another method to make colloidal silver is to electrolytically generate the silver colloids in some other toxic electrolyte such as $H_2SO_4$ (toxic) or citric (nontoxic) acid solution, etc., or by arcing between two electrodes submersed in distilled water.

It is an object of this invention to provide an improved bacteriostatic agent which is effective against bacterial, fungi, and viral pathogens.

It is a further object of this invention to provide more effective ways to produce greater concentrations of ionized metals such as ionized silver (and ionizations of other precious metals) for use as bacteriostatic agents.

It is a further object of this invention to make ionized metals such as ionized silver (and ionizations of other precious metals) for use as bacteriostatic agents by using electrolysis in organic acids wherein one or more of said organic acids is the electrolyte for the electrolysis process.

It is another object of this invention to produce an organic acid, such a fulvic acid, for use as an electrolyte in the production of bacteriostatic agents from precious metals, such as silver.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims.

BRIEF SUMMARY OF THE INVENTION

The above-noted problems, among others, are overcome by the present invention. Ionized metals such as ionized silver (and ionizations of other precious metals such as, but not limited to gold, platinum, palladium, and other platinum group metals, for example, are effective wide-spectrum bacteriostatic agents against bacteria, fungi, and viruses. Organic acids such as fulvic acid, humic acid, and ulmic acid also have bacteriostatic properties. Ionizing these metals in the organic acids identified above amplifies and increases the known benefits of the dissolved metal ions or colloids or products of reaction that are formed in the acids. The preferred organic acids of fulvic acid, humic acid and ulmic acid are natural chelating and reactive agents which combine with the colloidal silver formed by electrolysis to form non-toxic compounds.

The organic acid based compositions also produce greater stability of silver ions in solution. It has been known that fulvic acid is a highly oxidized, biologically stable, water-soluble naturally occurring complexing agent that can complex di- and trivalent metal ions and hydroxylated metal compounds. It has also been hypothesized that a possible explanation for the experimental results on increased root development lies in the power of the fulvic acid to form stable water-soluble complexes with divalent and trivalent metals ions. It has been reported by the Jackson reference that aquatic humus is composed predominantly of fulvic acid material with a molecular weight of less than 700. Such low molecular weight fractions are able to chelate or complex two to six times more metal than other higher molecular weight fractions.

In the electrolytic generation of silver ions (and ionizations of other precious metals and precious metal colloids) ionization is produced electrolytically in a solution of a organic acids having no known toxicity to higher life forms. Preferred organic acids are humic acid, fulvic acid, ulmic acid, and mixtures thereof. When prepared in this manner (i.e., electrolytically with the organic acid as the electrolyte and the precious metal as the sacrificial electrode), the ionized metals produced—and especially ionized silver—are more effective bacteriostatic agents against a wide spectrum of pathogenic bacteria, fungi, and viruses. Since fulvic acid, humic acid, and ulmic acids are also bacteriostatic agents, a synergistic effect results from such combination and, as so combined, they amplify and increase the known benefits of the ionized metals, metal colloids, and other reactive products contained therein.

These organic acids are naturally occurring substances which are capable of vary active chelation of all monovalent and di-valent metals. Being of natural occurrence, utilized as electrolytes with one or more precious metals as anode (non-sacrificial electrode) and one or more precious metals as cathode (sacrificial electrode), these acids assist in cell nutrient transfers, as well as being strong anti-oxidants capable of detoxifying various pollutants. They can also increase enzyme activity and can act as both a donor or an acceptor in supplying balance to a cell.

The organic acids used in the present invention are preferably fulvic acid, humic acid, and ulmic acid. These acids are derived from decayed material known as humus and can be found in Leonardite ore. These materials are described by J. B. Aitken, et al., in "The Characteristics and Effects of Humic Acids Derived from Leonardite" in Technical Bulletin 1015: South Carolina Agriculture Experimental Station, Clemson University, Clemson, S.C. (hereafter referred to as Aitken). In brief, Aitken states the acids are obtained by the fractionation of organic matter. A dilute sodium hydroxide (2% solution) separates humus as a colloidal sol from alkali-insoluble plant residues. From this humus sol the humic fraction is precipitated by acid, which leaves a straw-yellow supernatant, the fulvic fraction. The alcohol soluble portion of the humic fraction is generally named ulmic acid. The average molecular weight of the humic acids is believed to be between 5,000 and 50,000. They have no definite x-ray or electron diffraction and are presumed to be amorphous.

The amount of silver ions in most colloidal solutions, however, represents a small percentage of the total silver in the colloid. In U.S. Pat. No. 2,785,154, Lock, et al., discloses an estimate of the relative amounts of silver in a 10% solution of mild silver protein. The total silver content is near 20 mg./ml, but only 0.000001 to 0.00001 mg per ml is ionized (the active form). The same ratio is given in Locke, et al. 's U.S. Pat. No. 2,785,153. Other silver colloid preparations reflect a comparable ratio of silver ions to total silver. The present invention permits higher silver ion concentrations to form reactants believed capable of accessing intercellular pathogens. By using the process of the present invention using fulvic, humic or ulmic acids as electrolytes high metal ionic concentrations are combined as non-toxic, chelated or solution reactants. Effective compositions are produced having metal ion concentrations varying from less than 1 ppm to several thousand ppm.

The process of this invention ties the in situ produced silver ions and other ions of other precious metals to naturally occurring organic acids yielding significantly higher concentrations of reaction products of known beneficial and pathogenic uses (i.e., ionized silver).

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

DETAILED DESCRIPTION OF THE INVENTION

The first phase of the process of this inventions is to prepare a solution of fulvic acid, humic acid, or ulmic acid as described herein. These solutions may be single acid solutions (i.e., fulvic acid only, humic acid only, or ulmic acid only) or may be combinations of two or more of the acids in solution. The concentration may vary in strength from very weak (500 ppm) to very strong (36,000 ppm)—such ranges, and any ranges in between, are suitable for my inventive method. It is preferred, however, that fulvic acid, ranging in strengths of between about 3,500 ppm to about 4,500 ppm, more or less, be used. The preferred precious metal as an electrode is silver.

These organic acids are not generally available at commercial chemical supply stores but may be obtained from large industrial agricultural manufactures such as Live Earth Products at P.O. Box 76 in Emery, Utah, 84522; and Medina Agricultural Products, Inc., A Division of Medina Products at P.O. Box 309, Highway 90 West, in Hondo, Tex., 78861. Technically, fulvic acid is not a single acid but consists of a number of organic acids which have been classified by scientists into one group having similar physical and chemical characteristics. Although the term 'fulvic acid' is commonly used in the field and in the literature , the term actually embraces the plural instead of the singular; i.e., fulvic acids is the most technically correct, but fulvic acid is the generally accepted norm. For administrative clarity, I will use the common term 'fulvic acid' throughout to represent 'fulvic acids'.

Basically, fulvic acid is extracted from Leonardite ore which still contains fulvic acid. Initially Leonardite ore does contain fulvic, but, over time the fulvic content will leach out. The common process is a water extraction process which first entails grinding Leonardite ore to about 20 mesh or less. The ground ore is placed into a cylinder having an open top and a filtered bottom discharge for the water. The cylinder is like a strainer filled with the ground ore. Water is poured through the cylinder and fulvic acid, and other water-soluble minerals and trace elements, such as iron, calcium, and aluminum, for example, leach out of the ground ore as they combine with the water.

The initial fulvic extract contains high concentrations of fulvic acid in combination with iron, calcium, and aluminum (up to about 36,000 ppm). The ore also still contains sufficient amounts of fulvic acid which, after the first extraction process, is followed by additional extractions in the same manner; i.e., after basically all the water (containing fulvic acid and the other water-soluble minerals) leaches out of the cylinder and the fulvic extraction is captured (fulvic extract); more water is poured into the cylinder which extracts more fulvic acid (at less concentrations than a previous extraction) and the other water-soluble minerals described above.

With each successive extraction, less and less fulvic acid is extracted and, concomitantly, less and less other water-soluble minerals. Certain fractions of fulvic acid, known to the industry as 'golden fulvic', do not become water-soluble until after the water-soluble iron and calcium are leached from the ground ore; which is realized in the initial stages of the leaching operation. Once these interfering elements are removed, the golden fulvic, in combination with any soluble trace elements (such as sulfur, silicon, tellurium, cecium, potassium, boron, beryllium, bromine, copper, and manganese) that may be organically complexed with the golden fulvic fraction, may also go into solution and to be removed from the ground ore. When as much of the fulvic acid is extracted from the ground ore as is feasible (physically or economically), the extracts are combined into a final fulvic solution and then stabilized so that the minerals and the fulvic acid therein do not precipitated out and thereby diminish the agricultural value of the fulvic solution. The fulvic acid concentrations can vary in this final fulvic solution from 500 ppm to as high as 10,000 ppm depending upon the manufacturer and the process used.

Most commercial manufacturers or producers of fulvic acid use citric acid to facilitate leaching and, therefore, generally have not need to stabilize the final fulvic solution with ascorbic acid. They will, however, generally use sodium benzoate to inhibit mold. The volume of sodium benzoate used will vary from between 0.01% to 0.10%, depending on the source of humic material initially used.

Otherwise, stabilization entails first adding sodium benzoate (to inhibit mold) and ascorbic acid (to prevent the precipitation and 'drop-out' of iron, calcium, aluminum). To realize these stated and desired purposes, the ratio of sodium benzoate is such that it comprises approximately 0.01% to 0.1% by volume of the total fulvic solution and the ratio of ascorbic acid is such that it comprises approximately 0.0001% by volume of the total fulvic solution. As the iron and calcium content of a fulvic solution may vary, depending on the source or raw materials, the amount of ascorbic acid necessary to stabilize the fulvic solution may also have to be increased or decreased accordingly.

For administrative clarity, I will refer the fulvic solution which is commercially obtained as Solution 1. Solution 1 is suitable for use as an electrolyte but, because of the minerals contained within Solution 1; i.e., calcium, iron, and aluminum, the results of producing ionized silver (or ionizations of other precious metals) are not as good as results which are obtained from using fulvic solutions stabilized and prepared in a manner I have crafted which is different from the commercial manner (i.e., Solutions 1 and 2). Refer to Table I (which follows this disclosure), Column A for Solution 1 results, and to Columns B and C for Solution 2 and Solution 3 results, respectively. Solution 1 as an electrolyte did not start taking silver into solution until 14.5 hours after start of electrolysis.

The typical electrolysis process entails using fulvic acid, or fulvic solution as I refer to it herein, as an electrolyte; using one precious metal (preferably silver) as a sacrificial electrode, and using as a non-sacrificial electrode either silver of about the same size or surface area as the sacrificial silver electrode or an inert non-precious metal (such as, but not limited to, USP grade titanium, graphite carbon, compounds of stainless steel [excepting 303]) of about twice the size or surface area of the sacrificial silver electrode. Using as the sacrificial electrode, either pure silver (0.999 pure) or such silver alloyed with a small amount (between approximately 0.001 to 0.10% by weight of the alloy) of another precious metal, such as, but not limited to, gold or palladium or any precious metal provided such is below silver in the electromotive series, can enhance and increase the germicidal and oligodynamic effects of ionized silver; provided, the alloy used is below silver in the electromotive series. The reason for basically doubling the size or surface area of the non-sacrificial electrode when silver is not used as the non-sacrificial electrode is because silver is a good conductor. The other metals used are not as good. I, therefore, try to match or bring the conductance of the non-silver non-sacrificial electrode to that of the silver sacrificial electrode. Doubling the size or surface area of this non-sacrificial electrode accomplishes this purpose.

For the results reflected in Table I, in a tank containing approximately 9000 ml fulvic solution, I used a bar of fine silver comprising 0.999 silver and containing approximately 0.01% gold as the sacrificial electrode. The dimensions of the silver bar were 2.5 mm thick, 16.0 mm tall, and 4.5 mm wide comprising a total surface area of about 246.5 sq. mm. As the non-sacrificial electrode, I used a plate or sheet of USP titanium measuring significantly larger than the size or surface area of the silver bar; i.e., 0.25 mm thick, 9.0 mm wide, and 16.0 mm tall comprising a total surface area of about 300.5 square mm (if silver is used as the non-sacrificial electrode, it should be about the same size as the sacrificial [silver] electrode). Each electrode was submerged in the electrolyte such that the submerged surface area of the sacrificial electrode [silver] comprised about 172.25 square mm; and the submerged surface of the non-sacrificial electrode [titanium] comprised about 259 square mm. The ratio of surface-area to volume-per-ml for each electrode was about 0.0191:1 for the sacrificial electrode and about 0.0287:1 for the non-sacrificial electrode (if, however, the non-sacrificial electrode were of the same material as the sacrificial electrode [silver in this example], the ratio for the non-sacrificial electrode would be about the same as it is for the sacrificial electrode.

The electrodes are spaced apart (in the configuration described above and using the surface areas in solution described above, spacing was approximately 25.5 mm). Spacing, however, is relative to volume of electrolyte and size or surface area of the electrodes. An external power source is applied to the electrodes which supplies power at a current density of about 2 volts or more (I used 12 volts for the examples set forth in Table I) at up to 2.0 amps. For the results shown in Columns A and B, voltage was set at 12 with amperage at 0.2 amps.

For good results, I have found the ratio between surface area of the sacrificial electrode per square mm to solution per ml should be between about 0.008 to 0.080 square mm per 1 ml solution. Better results are obtainable when such ratio is between about 0.010 to about 0.040 per 1 ml solution; with best results when such ratio is about 0.019 per 1 ml solution. As to the ratio between the surface area of the non-sacrificial electrode (when it is not of the same material as the sacrificial electrode) per square mm to solution per ml; good results are attained when such ratio is between about 0.010 to 0.100 square mm per 1 ml solution. Better results are obtainable when such ratio is between about 0.020 to about 0.050 per 1 ml solution; with best results when such ratio is about 0.029 per 1 ml solution.

I have found that much better results are achieved when, all else being the same, after the extraction process as explained above has concluded, stabilization entails applying the stabilizing components (sodium benzoate and ascorbic acid) in reverse order; i.e., applying ascorbic acid (between about 0.00001% to about 0.001% by volume; or about 0.0001% by volume) first followed by application of sodium benzoate (between about 0.01% to about 0.10% by volume). This is followed by allowing the fulvic solution (referred to herein as Solution 2) to stand for approximately 24 hours to permit flocculent minerals (calcium, iron, and aluminum) to settle and be removed leaving a relatively clear, aqueous stabilized fulvic solution as the electrolyte.

Following this method of stabilizing the fulvic solution causes most of the calcium, iron, and aluminum to precipitate out of solution which, in commercial preparations and applications, is not desirable as these minerals are well suited for agricultural purposes. In my unique process of using fulvic acid as an electrolyte for the ionization of precious metals, it is preferred that these minerals be out of solution (forming what I have referred to as Solution 2). Refer to Table I, column B, for the ionization results using Solution 2, with all other factors equal. These results reflect a significant reduction in time of processing and a drastically increased concentration of ionized silver.

I have achieved even better results when cations are also extracted from solution (forming what I refer to as Solution 3). Even when a commercially obtained fulvic solution is used, if cations are removed, Solution 3 is formed thereby, and greater results are realized. In this regard to form Solution 3 from Solution 1, Solution 1 (commercially obtained fulvic acid already stabilized) should be run through any commercially available ion-exchange column (or any suitable ion-exchange column) which contain, or into which are added, resins for the process (resins such as, but not limited to, Doulite/Amberlite IR 120+H resins manufactured by Rohm & Haas). In this process, Solution 1 is pumped to the top of the cylinder of the Rohm & Hass ion-exchange column and is allowed to migrate down the column through the resin bed after which the solution is discharged into a receiver at the bottom of the column. Cations are thereby removed and Solution 3 is created and then used as the electrolyte. Refer to Table I, Column C for the results on ionization using Solution 3 as the electrolyte, voltage at 12 (amperage increased to 0.8 amps due to the fact that cations were removed from solution leaving far less dissolved minerals in solution acting as an electrolyte thereby requiring greater amperage to force current through solution to the non-sacrificial electrode).

Testing of the electrolyte for ionization results reflected in Table I was performed every one-half hour using a 306 Perkin Elmer Atomic Absorption Spectrophotometer. Solution 1 did not start registering the presence of silver in solution until 14.5 hours into the electrolysis. It seems that, after the initial conditioning of the electrolyte (about one-half hour), colored precipitates became visible as finely divided mineral particles dispersed throughout the electrolyte and continued to slowly precipitate until about 14.5 hours into the process; at which time atomic absorption tests of the electrolyte showed that the electrolyte had started taking silver into solution. Physical observation revealed that almost total precipitation of iron, calcium, and aluminum was required before the electrolyte began taking on silver. After about 100 hours, the concentration of ionized silver reached 258 ppm. See Table I, Column A. This can vary depending on the provider of the fulvic acid but not by much.

The absence of these interfering elements in Solution 2 represents a dramatic improvement in yield (Table I, Column B), as does removal of cations (Table I, Column C). Table I, Column D reflects use of Solution 3 but doubled in volume (size of electrodes being the same as previously described for columns A through C), voltage the same, but, because of conductivity issues, amperage increased to 1.0 amps. Results here were significantly diminished as compared to the results of Columns B and C.

In the electrolysis process described, two or more eletrodes may be used. Generally only two are necessary; one as an anode, one as a cathode. The electrodes are introduced into the fulvic solution (Solution 1, Solution 2, or Solution 3). The composition of the eletrodes can be the sacrifical electrode of the desired metal and the other electrode can be of a non-contaminating metal or substance. The use of the same metal for both electrodes is a guard against any impurities contamination which could be intruduced by the non-sacrificial electrode. Although use of the same metal for both electrodes is the preferred method, inert substances such as graphite carbon compounds of stainless steel electrodes (excepting 303) or USP grade of titanium can be used as the non-sacrificial electrode.

Each eletrode is connected to the positive or negative leads of a DC power source or a DC power source which may be of the continous, puled or superimposed AC type. The current density and the distance between the electrodes can be varied in any suitable comination to satisfy the demands of the desired end-product. Distance between electrodes can vary from millimeters to meters and is relevant to the desired end-product. Distance, however, should be relative to the distance described previously herein in relation to the volume of the electrolyte and the size/dimensions of the electrodes. Desirable metal solution concentrations of the end-product can be controlled by time duration of electrolysis coupled with other variable parameters. Metal ion concentration can vary from less 1 ppm to several thousand ppm as illustrated in Table I.

After the desired concentrations of ionized silver have been realized, the preferred next step is a allow the colloids in solution to settle for a period of time sufficient to allow their settlement and that of any fragmented, undissolved over-size particles. Using any conventional unit suited for the intended purpose (such as, but not limited to an atomic absorption spectrophotometer), I prefer to test the amounts of silver in solution during the settlement process and, as the colloidal silver drops out of solution, progressive atomic absorption testing shows a decline in total silver content of the solution until a stable reading is obtained; at which time virtually all of the colloidal silver is absent from solution leaving only ionized silver remaining which then can be removed. The ionized silver may be pumped out or siphoned out and by any suitable means such that the sediment of colloidal silver is not disturbed—to thereby prevent its mixing with the ionized silver being removed.

Near the end of the removal process, some sediment will mix with the ionized silver. Further refining of this product can be achieved by filtering through a micron filter such as the Hydrex II GX01–GX05, produced by Osmonics Inc. of Minnetonka, Minn. Even the initially removed ionized silver may be run through a micron filter to further ensure its purity.

This entire procedure can be used to produce colloids, ionizations, and other reaction products of silver, gold, the platinum group metals (i.e., platinum, palladium, rhodium, osmium, ruthenium, and iridium), and any other metals that may prove beneficial. Other base metals such as zinc, copper, and mercury can be used, but the preferred metals are the precious metals with silver proving to be the best suited.

Base metals are discussed by the Becker reference at page 163, wherein the effects of a variety of metallic electrodes on several different types of bacteria in culture was tested. Each metal was tested at voltages ranging from very small to just above the electrolysis level. It was found that about the electrolysis level, positive metal electrodes (anodes) killed all bacteria, but they would have also killed any human cells. Only the silver anode killed all bacteria at voltages that would be harmless to human cells. Becker thus shows that positive base metal electrodes killed all bacterial, but that at the current densities necessary to produce such base metal ions (in vivo), the base metal electrodes would have also killed any human cells. In the present invention, this problem is not encountered since the metal ions are not produced in vivo, but are ionized in the non-toxic electrolyte media and then used for specific applications. The Reddish reference also discusses base metals in "Antiseptics, Disinfectants, Fungicides and Chemical and Physical Sterilization" at page 487 and at page 491.

These colloids and/or metal ions and solution reactants serve as antibiotic, antiviral and antifungal agents. Studies confirming these abilities are also cited in the Reddish reference at page 470. At page 482, there is also reference made concerning the benefits of adding small amounts of other precious metals to silver. It stated: "Krause described it as spongy lamellar, metallic form of pure silver to which is added an activating metal below silver in electropotential series, such as palladium or gold." Studies cited in the Reddish reference, at pages 471–477, clearly identify that it is the silver ion which is the most active factor of any silver preparation in its bacteriostatic benefits. None of the prior art references discusses production of ionized precious metals, particularly silver, by using organic acids, particularly fulvic acid, as an electrolyte and the precious metals used as electrodes, nor of using fulvic acid as prepared and stabilized by the process of the present invention and thereafter used as an electrolyte There are may advantages to using fulvic acid, humic acid or ulmic acid as the electrolyte. The prior art use of protein silver colloids which are precipitated and chelated from silver nitrate carries with it the toxic nitric factors which reduce the level of safe use. In the present invention, by using an organic acid which reacts with the silver or other metal ions, this carries no toxic factors and thus produces a safer product at comparable concentrations.

The product of the present invention also permits the more complete assimilation of silver into the body. For example, consider the use of fulvic acid only. In the Jackson reference, supra, at page 250, there is a discussion of the advantages of fulvic acid with living matter. These advantages include enhanced cell permeability, pH buffering capacity, ability to establish chemical balance to cells, ability to stimulate cell metabolism, positive effect on RNA and DNA, and the ability to add other important nutrients to the cell. These benefits are natural to fulvic acid, and as it complexes with silver ions it thus greatly assists the assimilation of silver into the cells. The fact that viruses replicate within the cell and that the silver ions form reactants within the structure of fulvic acid which can access the inside of the cell opens the possibility of a more positive response to interviral infections.

The product of this invention is a significant improvement over the prior art of producing silver protein by the precipitation of silver from silver nitrate solutions. Dilute silver protein solutions do not eliminate the toxic nitrate factor, but do buffer it. The nitrate factor remains a strong irritant when present in either mild or strong silver protein. The reaction of the silver ion into the structure of the fulvic, humic or ulmic acids according to the present invention introduces no toxic substances and no irritant factor to the final product.

A further advantage of the product of this invention is that it eliminates the necessity of stabilizing the colloidal silver with synthetic chelating agents. These coatings may interfere with the metal ions ability to interact with its surrounding and may prevent the ionized particle from fully accessing body cells and tissues. It may also cause chemical interference from the protein coatings or chelating agent itself. In the present invention the metal ions are complexed with a natural electrolyte which has the potential to enter cells and tissues to enhance cell nutrition. The result is an improved delivery system for the silver ion.

Having described the basic aspects of the invention, the following examples as taken from Table II (which follow the examples) are given to illustrate specific embodiments thereof.

EXAMPLE 1

This example illustrates the production of a solution of humic acid and electrolytic silver. Humic acid was obtained by extracting it from Leonardite according to the procedure described by J. B. Aitken et al. in "The Characteristics and Effects of Humic Acids Derived from Leonardite" in Technical Bulletin 1015: South Carolina Agriculture Experimental Station, Clemson University, Clemson, S.C. Silver was added by the procedure described earlier in the section Electrolysis Process Embodiment and the silver concentration was 200 ppm.

EXAMPLE 2

This example illustrates the production of a gel form of fulvic acid and electrolytic silver. Fulvic acid gel was obtained by extracting it from Leonardite according to the procedure described by J. B. Aitken et al. in Example 1. Silver was added by the process referenced in Example 1 and the silver concentration was 200 ppm. Carrageenan (Irish Moss) was then blended in to form the final gel.

EXAMPLE 3

This example illustrates as a comparison the production of half strength fulvic acid (4,000 ppm) with no electrolytic silver. Fulvic acid as 4,000 ppm with no silver added was prepared by extracting it from Leonardite according to the procedure described by J. B. Aitken et al. in Example 1. It was concentrated to 8,000 ppm and then diluted with distilled water to 4,000 ppm.

EXAMPLE 4

This example illustrates the production of a solution of fulvic acid and electrolytic silver and gold. Fulvic acid was prepared by extracting it from Leonardite according to the procedure described by J. B. Aitken et al. in Example 1 to a concentration of 4,000 ppm. It was concentrated to 8,000 ppm. Gold and silver were added by the procedure described earlier in the section Electrolysis Process Embodiment with the silver concentration being 200 ppm and the gold concentration being 6 ppm. A sample of this material was then diluted with distilled water to 4,000 ppm and it is identified as Example 4a. The sample contained 100 ppm silver and 3 ppm gold.

EXAMPLE 5

This example illustrates the production of a solution of fulvic acid and electrolytic silver. Fulvic acid was prepared by extracting it from Leonardite according to the procedure described by J. B. Aitken et al. in Example 1 to a concentration of 8,000 ppm. Silver was added by the procedure described earlier in the section Electrolysis Process Embodiment and the silver concentration was 200 ppm. A sample of this material was then diluted with distilled water to 4,000 ppm and it is identified as Example 5a. The sample contained 100 ppm silver.

EXAMPLE 6

This example illustrates the effectiveness of these solutions in bacteriostatic activity. The solutions from Examples 1–4 were used to treat *E. Coli, Staph Aureus* and *Candida Albicans*. The control experiment has *E. Coli* at 200 pathogen count per culture, *Staph Aureus* at 80 and *Candida Albicans* at 20. The results are set forth in Table II.

TABLE I

| Time (in hours) | COLUMN A Solution 1 (PPM) | COLUMN B Solution 2 (PPM) | COLUMN C Solution 3 (PPM) | COLUMN D Solution 3 (PPM) |
|---|---|---|---|---|
| 0.5 | 0 | 0 | 83 | 15 |
| 1.0 | 0 | 0 | 156 | 34 |
| 1.5 | 0 | 0 | 234 | 45 |
| 2.0 | 1 | 1 | 319 | 55 |
| 2.5 | 0 | 0 | 402 | 69 |
| 3.0 | 0 | 11 | 488 | 82 |
| 3.5 | 2 | 27 | 535 | 87 |
| 4.0 | 1 | 62 | 658 | 108 |
| 4.5 | 0 | 76 | 730 | 134 |
| 5.0 | 0 | 199 | 839 | 150 |
| 5.5 | 1 | 234 | 940 | 224 |
| 6.0 | 0 | 240 | 1088 | 290 |
| 6.5 | 0 | 358 | 1268 | 329 |
| 7.0 | 0 | 471 | 1489 | 446 |
| 7.5 | 0 | 623 | 1736 | 488 |

TABLE I-continued

| Time (in hours) | COLUMN A Solution 1 (PPM) | COLUMN B Solution 2 (PPM) | COLUMN C Solution 3 (PPM) | COLUMN D Solution 3 (PPM) |
|---|---|---|---|---|
| 8.0 | 1 | 804 | 2017 | 533 |
| 8.5 | 0 | 1016 | 2314 | 552 |
| 9.0 | 1 | 1341 | 2639 | 569 |
| 9.5 | 1 | 1703 | 3027 | 615 |
| 10.0 | 2 | 2115 | 3515 | 637 |
| 14.5 | 17 | 2167 | 3562 | — |
| 20.0 | 38 | 2138 | 3527 | — |
| 30.0 | 67 | 2180 | 3498 | — |
| 100.0 | 258 | 2309 | 3618 | — |

TABLE II

| Example | E. Coli Conc. | E. Coli % reduced | Staph Aureus Conc. | Staph Aureus % reduced | Candida Albicans Conc. | Candida Albicans % reduced |
|---|---|---|---|---|---|---|
| control | 200 | | 80 | | 20 | |
| 1 | 0 | 100 | 39 | 51.3 | 3 | 85 |
| 2 | 33 | 83.5 | 25 | 68.8 | 1 | 95 |
| 3 | 27 | 86.5 | 24 | 70 | 2 | 90 |
| 4 | 0 | 100 | 44 | 45 | 6 | 70 |
| 4a | 0 | 100 | 12 | 85 | 2 | 90 |
| 5 | 0 | 100 | 17 | 78.8 | 0 | 100 |
| 5a | 0 | 100 | 14 | 82.5 | 1 | 95 |

The present disclosure includes that contained in the present claims as well as that of the foregoing description. Although this invention has been described in its preferred forms with a certain degree of particularity, it is understood that the present disclosure of the preferred form has been made only by way of example and numerous changes in the details of construction and combination and arrangement of parts and method steps may be resorted to without departing from the spirit and scope of the invention. Accordingly, the scope of the invention should be determined not by the embodiment[s] illustrated, but by the appended claims and their legal equivalents.

I claim:

1. A process for producing organic acids for use as an electrolyte in producing high ionization concentrations of precious metals comprising the steps of:

(a) obtaining commercially produced fulvic acid as the organic acid of choice; and (b) removing cations from said fulvic acid wherein said fulvic acid content with said cations removed ranges from between about 500 ppm to about 36,000 ppm.

2. The process as defined in claim 1 wherein removal of said cations from said fulvic acid comprises running said fulvic acid through an ion-exchange column containing resins and collecting the cation-free solution thereafter.

3. The process as defined in claim 1 further comprises using said fulvic acid as an electrolyte in producing high ionization concentrations of precious metals.

4. A process for producing organic acids for use as an electrolyte in producing high ionization concentrations of precious metals comprising the steps of:

(a) obtaining commercially produced fulvic acid as the organic acid of choice;

(b) removing cations from said fulvic acid; and (c) using said fulvic acid as an electrolyte in producing high ionization concentrations of precious metals.

5. The process as defined in claim 1 wherein said fulvic acid content with cations removed ranges from between about 500 ppm to about 36,000 ppm.

6. The process as defined in claim 1 wherein removal of said cations from said fulvic acid comprises running said fulvic acid through an ion-exchange column containing resins and collecting the cation-free solution thereafter.

* * * * *